United States Patent
Gong et al.

(10) Patent No.: US 12,315,274 B2
(45) Date of Patent: May 27, 2025

(54) MULTI-SENSOR DEVICE FOR DIETARY TRACKING

(71) Applicant: Foodfx Inc, San Jose, CA (US)

(72) Inventors: Fengmin Gong, Los Altos Hills, CA (US); Weijun Zhang, San Jose, CA (US); Min Fan, Bellevue, WA (US); Jun Du, Cupertino, CA (US)

(73) Assignee: Foodfx Inc, San Jose, CA (US)

( * ) Notice: Subject to any disclaimer, the term of this patent is extended or adjusted under 35 U.S.C. 154(b) by 341 days.

(21) Appl. No.: 17/555,745

(22) Filed: Dec. 20, 2021

(65) Prior Publication Data
US 2023/0196802 A1    Jun. 22, 2023

(51) Int. Cl.
*G06V 20/68* (2022.01)
*G16H 20/60* (2018.01)

(52) U.S. Cl.
CPC ............. *G06V 20/68* (2022.01); *G16H 20/60* (2018.01)

(58) Field of Classification Search
CPC ........ G06V 20/68; G06V 10/82; G06V 20/52; G06V 10/764; G16H 20/60; G16H 40/63; G16H 40/67; G01N 33/02; H04M 2250/52; G06N 20/00; G06N 3/045; G06N 3/02; G06F 18/24; G06F 3/0482; G06F 18/2415; G06T 2207/30128; G06T 2207/10024; G06T 7/50; G06T 2207/10028; G06T 2207/20081; G06T 7/90

See application file for complete search history.

(56) References Cited

U.S. PATENT DOCUMENTS

| | | | | |
|---|---|---|---|---|
| 2015/0168365 A1* | 6/2015 | Connor | ............... | A61B 5/681 |
| | | | | 356/402 |
| 2015/0228062 A1* | 8/2015 | Joshi | .................. | G06Q 50/12 |
| | | | | 382/110 |
| 2016/0063734 A1* | 3/2016 | Divakaran | ........... | G06V 10/50 |
| | | | | 382/110 |
| 2016/0150213 A1* | 5/2016 | Mutti | .................. | G06V 20/20 |
| | | | | 348/143 |
| 2019/0290172 A1* | 9/2019 | Hadad | ................ | A61B 5/0022 |
| 2021/0365687 A1* | 11/2021 | Starson | .............. | G16H 20/60 |

OTHER PUBLICATIONS

Lo, F.P.-W.; Sun, Y.; Qiu, J.; Lo, B. Food vol. Estimation Based on Deep Learning View Synthesis from a Single Depth Map. Nutrients 2018, 10, 2005. https://doi.org/10.3390/nu10122005 (Year: 2018).*

* cited by examiner

*Primary Examiner* — Gandhi Thirugnanam
*Assistant Examiner* — Aaron Joseph Sorrin
(74) *Attorney, Agent, or Firm* — Sheppard Mullin Richter & Hampton LLP

(57) ABSTRACT

Methods, systems, and apparatuses, including computer programs encoded on computer storage media, for dietary tracking with instant dietary feedback using a portable multi-sensor device are described. An example method may include: obtaining a first machine learning model trained based on a plurality of food images and corresponding labels; receiving a series of images from one or more cameras capturing a user taking food out of a food-serving storage; determining, using the first machine learning model based on the series of images, an identification of the food being taken by the user; determining, using a second machine learning model based on the series of images and the identification of the food, an estimated weight of the food being taken by the user; determining and displaying portion-based food information of the food being taken by the user.

19 Claims, 6 Drawing Sheets

MULTI-SENSOR DEVICE FOR DIETARY TRACKING

TECHNICAL FIELD

The disclosure generally relates to systems and methods for food servicing, specifically, an Artificial Intelligence (AI) assisted multi-sensor device and system for dietary tracking.

BACKGROUND

Traditional self-serve food services, such as cafeteria, buffet, banquet, or food market, lack the capability of providing users instant dietary feedback (e.g., portion-based nutrition information, allergen, or other suitable information) on the food being taken by the users, especially when the food is an unpacked form. In this disclosure, an AI-assisted multi-sensor device is described to provide users instant dietary feedback with precise food information. The instant dietary feedback will provide users better understandings of the to-be-consumed food in real-time and allow the users to adjust the portion size accordingly.

SUMMARY

Various embodiments of the present specification may include systems, methods, and non-transitory computer-readable media for providing instant dietary feedback using an AI-assisted multi-sensor device.

According to a first aspect, a computer-implemented method for dietary tracking with instant dietary feedback is described. The method may include obtaining a first machine learning model trained based on a plurality of food images and corresponding labels; receiving a series of images from one or more cameras capturing a user taking food out of a food-serving storage; determining, using the first machine learning model based on the series of images, an identification of the food being taken by the user; determining, using a second machine learning model based on the series of images and the identification of the food, an estimated weight of the food being taken by the user; determining, based on the identification and the estimated weight of the food, portion-based food information of the food being taken by the user; displaying the portion-based food information of the food to the user; receiving an actual weight of the food from one or more weight sensors when the user places the food on the scale; updating the portion-based food information of the food being taken by the user based on the identification and the actual weight of the food; and displaying the updated portion-based food information of the food to the user.

In some embodiments, the method may further include receiving the plurality of food images captured by the one or more cameras when an operator scans one or more food items using the one or more cameras; receiving the corresponding labels of the plurality of food images scanned by the operator; and training a neural network as the first machine learning model based on the plurality of food images and the corresponding labels for food identification.

In some embodiments, the neural network comprises a layer for feature extraction and an output layer, the output layer comprising one or more nodes corresponding to the one or more food items.

In some embodiments, the training of the neural network includes: inputting a food image into the neural network to obtain one or more matching probabilities corresponding to one or more matched food; and adjusting parameters of the neural network based on the one or more matching probabilities and a label corresponding to the food image.

In some embodiments, the series of images comprises one or more depth images of the food captured by the one or more cameras from one or more viewing angles.

In some embodiments, the determining the estimated weight of the food being taken by the user includes: inputting a first depth image of the food captured from a first view angle into the second machine learning model; receiving, from the second machine learning model, a second depth image of the food from a second view angle that is different from (opposite to) the first view angle; generating a 3D representation of the food being taken by the user based on the first depth image and the second depth image; obtaining an estimated volume of the food being taken by the user based on the 3D representation of the food; and determining the estimated weight of the food based on the estimated volume of the food and the identification of the food.

In some embodiments, the second machine learning model comprises a trained deep neural network.

In some embodiments, the determining the estimated weight of the food being taken by the user includes: obtaining food information of the food from a database based on the identification of the food; and determining the estimated weight of the food based on the food information and the estimated volume.

In some embodiments, the determining of the identification of the food being taken by the user includes: feeding the series of images into the first machine learning model to obtain one or more probabilities of one or more predicted identifications of the food; displaying the one or more predicted identifications on the display, with a first predicted identification with a highest probability being displayed as the identification of the food; and in response to a user selection of a second predicted identification from the one or more predicted identifications, updating the display by displaying the second predicted identification as the identification of the food.

In some embodiments, the method may further include: receiving a scanned menu from the one or more cameras; converting the scanned menu into text using Optical Character Recognition (OCR); extract food identifications and corresponding food information from the text using Natural Language Processing (NLP), wherein the food identifications comprise food names; and storing the food identifications and the corresponding food information in a database.

In some embodiments, the determining of the portion-based food information of the food being taken by the user includes: retrieving food information of the food from the database based on the identification, wherein the food information comprises nutrition information of the food; and determining the portion-based food information of the food based on the food information and the estimated weight.

In some embodiments, the one or more cameras comprising one or more of the following: a depth sensor, a time of flight (ToF) camera, or a Light Detection and Ranging (LiDAR) camera.

In some embodiments, the portion-based food information comprises: portion-based ingredient information; portion-based nutrition information; portion-based pricing information; or allergen information.

According to a second aspect, an AI-assisted dietary tracking device is described. The device may include a scale coupled with one or more weight sensors; one or more cameras; a display; and one or more processors coupled to the one or more weight sensors, one or more cameras, and display, and configured to: obtain a first machine learning model trained based on a plurality of food images and corresponding labels; receive a series of images from the one or more cameras capturing a user taking food out of a food-serving storage; determine, using the first machine learning model based on the series of images, an identification of the food being taken by the user; determine, using a second machine learning model based on the series of images and the identification of the food, an estimated weight of the food being taken by the user; determine, based on the identification and the estimated weight of the food, portion-based food information of the food being taken by the user; display the portion-based food information of the food on the display; receive an actual weight of the food from the one or more weight sensors when the user places the food on the scale; update the portion-based food information of the food being taken by the user based on the identification and the actual weight of the food; and display the updated portion-based food information of the food on the display.

According to a third aspect, a non-transitory computer-readable storage medium is described. The storage medium may be configured with instructions executable by one or more processors to cause the one or more processors to perform operations including: obtaining a first machine learning model trained based on a plurality of food images and corresponding labels; receiving a series of images from one or more cameras capturing a user taking food out of a food-serving storage; determining, using the first machine learning model based on the series of images, an identification of the food being taken by the user; determining, using a second machine learning model based on the series of images and the identification of the food, an estimated weight of the food being taken by the user; determining, based on the identification and the estimated weight of the food, portion-based food information of the food being taken by the user; displaying the portion-based food information of the food to the user; receiving an actual weight of the food from one or more weight sensors when the user places the food on the scale; updating the portion-based food information of the food being taken by the user based on the identification and the actual weight of the food; and displaying the updated portion-based food information of the food to the user.

These and other features of the systems, methods, and non-transitory computer-readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

DETAILED DESCRIPTION

The description is presented to enable any person skilled in the art to make and use the embodiments and is provided in the context of a particular application and its requirements. Various modifications to the disclosed embodiments will be readily apparent to those skilled in the art, and the general principles defined herein may be applied to other embodiments and applications without departing from the spirit and scope of the present specification. Thus, the specification is not limited to the embodiments shown but is to be accorded the widest scope consistent with the principles and features disclosed herein.

In this disclosure, an AI-assisted multi-sensor device is described to provide users instant dietary feedback on the food being placed on a food container (e.g., a plate or a tray) so that the users can track their dietary data in real-time and adjust their dietary behavior accordingly.

In some embodiments, the AI-assisted multi-sensor device described below may be used in various foodservice settings in which users take food from a food-serving storage (e.g., a food-well in a cafeteria or buffet, or another form of container hosting food for the users to take) at a food station and place the food on a container (e.g., a plate, a tray, a bag) for later consumption. The device may be placed near the food station to capture images (or videos) of the users' food-taking actions. Based on the captured images, the device may use various machine learning models to identify the food being taken by the users, estimate the portion size (e.g., weight or volume) of the food being taken by the users before the food is placed on the container, determine estimated portion-based food information (e.g., nutrition information and/or price of the portion of food taken by a user) based on the food identification and portion-size, and provide the users instant dietary feedbacks with the estimated portion-based food information. Based on the instant dietary feedback, the users may decide whether to proceed to take the food (e.g., placing the food on the container) or adjust the portion size (e.g., returning some or all of the food to the food-serving storage). This process is completely automated using various sensors such as weight sensors, image sensors (e.g., 2D cameras and/or 3D cameras), as well as one or more processors deployed in the device for local data processing using multiple machine learning models.

Figure 1:
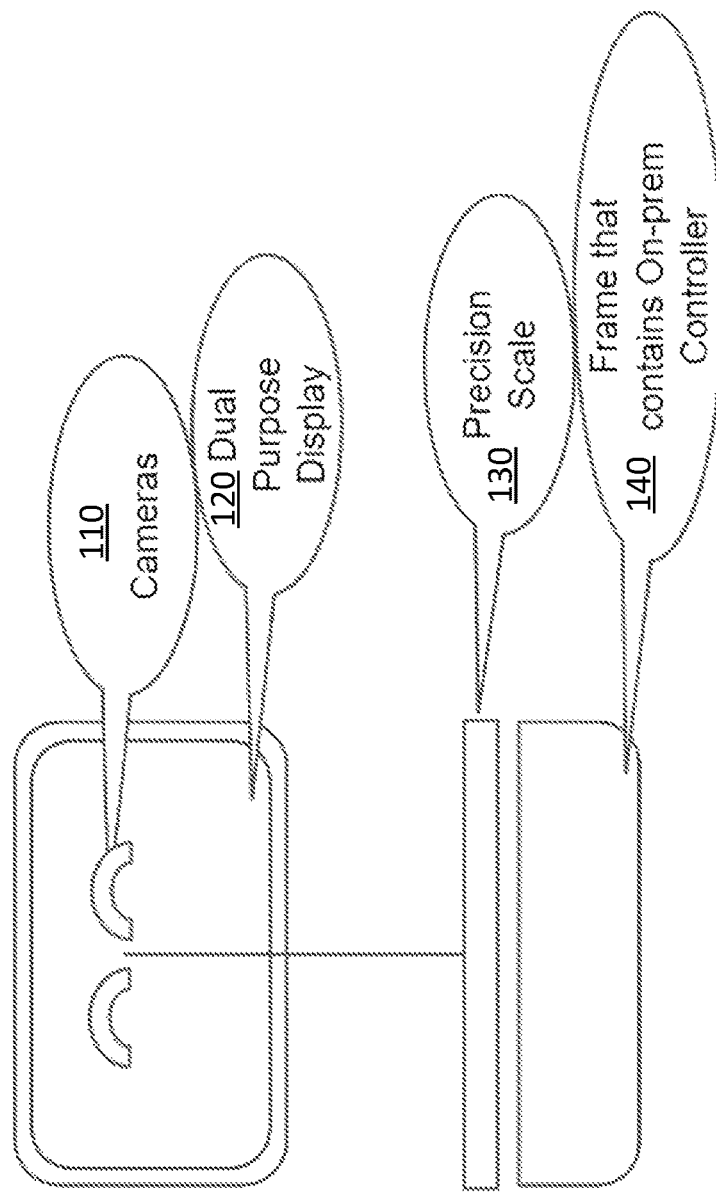
FIG. 1 illustrates an exemplary AI-assisted multi-sensor device for instant dietary feedback in accordance with some embodiments.

FIG. 1 illustrates an exemplary AI-assisted multi-sensor device 100 for instant dietary feedback in accordance with some embodiments. The structure and components of the device 100 in FIG. 1 are for illustrative purposes and may vary depending on the implementation.

As shown, the device 100 may include one or more cameras 110 for capturing images or videos. In some embodiments, the cameras 110 may have processors and internal storage storing trained machine learning models. These processors may use the machine learning models to locally process the captured images/videos, such as identifying objects (e.g., food) in the captured images/videos. These cameras 110 may be referred to as AI cameras in the following description. In some embodiments, these cameras 110 may perform preliminary data processing such as locating objects (e.g., food) in the images or videos using bounding boxes and send the bounding boxes to another computing device or other processors (e.g., an on-prem controller 140 of the device 100) to further identify the objects.

In some embodiments, the cameras 110 may include one or more of the following: a depth sensor, a time of flight (ToF) camera, or a Light Detection and Ranging (LiDAR) camera. The cameras 110 may capture 2D images, depth images, 3D point clouds, etc. In some embodiments, using deep learning models based on the depth images or the 3D point clouds generated by the cameras 110, the volume or weight of the food being taken by the user may be estimated. The estimated volume or weight may be sent to another computing device (e.g., the on-prem controller 140 of the device 100) to determine estimated portion-based food information. The estimated portion-based food information (e.g., nutrition, price) may be instantly displayed to the user. Based on the estimated portion-based food information, the user may timely adjust the portion size before placing the food onto a plate or container. This is practically helpful especially when the food is unpacked (e.g., in the forms of soup, stew, portage) and cannot be put back to the food serving storage once being placed on the plate. In these cases, the instant dietary feedback may help the user to avoid unknowingly taking an excessive amount of food.

In some embodiments, the device 100 may further include a dual-purpose display 120. The "dual-purpose" may mean the display 120 may be used as both an output and an input device. The display 120 may be used as an output device when it displays information to the users. The display 120 may be used as an input device when it is a touch screen and receives user input.

In some embodiments, the device 100 may further include a precision scale 130 equipped with one or more weight sensors (e.g., load cells). The precision scale 130 may be used to measure the weight of the food that has been taken by the user. For example, the user may place an empty plate on the precision scale. The precision scale 130 may measure the weight of the plate. When the user takes food from a food-serving storage and places the food onto the plate, the precision scale 130 may measure the total weight of the food and the plate, and thus determine the weight of food by subtracting the weight of the plate. The precise weight measurements may be sent to another computing device (e.g., the on-prem controller 140 of the device 100) to determine portion-based food information, such as the calorie amount in the portion of food taken by the user.

In some embodiments, the device 100 may further include a frame that contains an on-prem controller 140. The controller 140 may include one or more processors and non-transient storage media for conducting complex data processing based on the data received from the cameras 110, the dual-purpose display 120, and the precision scale 130. In some embodiments, the controller 140 may store one or more trained machine learning models and pre-configured pipelines (e.g., software programs). In some embodiments, the controller 140 may further include a database or have access to a database that stores food information (e.g., nutrition, price, allergen information indexed with food identifications).

For example, after a user takes food out of a food-serving storage using a serving utensil, but before the user places the food onto a plate (e.g., the plate is placed on the precision scale 130), the controller 140 may receive a series of images or a video capturing the movement around the food-serving storage. Based on the captured movement, the controller 140 may identify a food-taking action (e.g., taking food from the food-serving storage), a food-returning action (e.g., returning food back to the food-serving storage), or other suitable actions (e.g., a refilling action by an operator who refills the food-serving storage, a wiping action by an operator cleaning the spillovers). The actions may be identified by using a machine learning model based on the captured images of the movement. The machine learning model may extract various features from the captured images of the movement, such as the identification of the moving object (e.g., a food utensil with or without food therein), direction of movement (e.g., towards or away from the food serving storage), moving patterns (e.g., pouring food into the food-serving storage has a different moving pattern than returning a small amount of food back to the food-serving storage), and predict the action based on the extracted features. etc. For example, if the images of the movement contain a food utensil carrying food moving in a direction away from the food-serving storage, the action may be identified as a food-taking action. In contrast, if the images of the movement contain a food utensil carrying food moving towards the food-serving storage, the action may be identified as a food-returning action. The machine learning model may be trained based on user-collected data with proper labels. For example, one or more operators may perform various actions for the camera(s) to capture the movement images, and then label these movement images properly with the action names. For example, a set of movement images corresponding to the same action may share one label. Subsequently, these sets of movement images with corresponding labels may be used to train the machine learning model.

In response to the detected action being a food-taking action, the controller 140 may use an image recognition machine learning model trained based on food images and proper labels to identify the food in the utensil (e.g., based on the movement images capturing the utensil). Using a deep learning model, the controller 140 may estimate the volume or weight of the food in the utensil (more details in the descriptions for FIG. 3). Based on the food identification and the estimated volume or weight, the controller 140 may retrieve the corresponding food information from the database based on the food identification and thereby determine the portion-based food information based on the estimated volume or weight.

In some embodiments, the device 100 may further include interfaces for scanning unique identifications associated with users, such as RFID readers and antennas, QR code scanners (e.g., may use the cameras 110), Near-field communication (NFC) readers, or another suitable interface. User identification may be associated with the user's dietary data to provide personalized dietary tracking. For instance, a user may take food from multiple food stands at a banquet. The portion-based food information of the food taken by the user at each food station may be associated with the user identification and stored in the on-prem controller 140 or a cloud server. This food information may be aggregated and accumulated to reflect the user's food-intake activity at the banquet. The food information may also be collected and logged for a longer period (e.g., a week or a month) for later data analytics.

The practical applications of the device 100 include automatically identifying food, estimating portion-based food information, and providing users instant dietary feedback so that the user is more mindful about the food to be consumed. In some cases, the instant dietary feedback may help the user achieve a healthy diet, as well as notify the user about food safety concerns (e.g., by notifying the user about the allergens in the food or expiration date of the food). In some embodiments, instant dietary feedback may be offered to the user before the user places the food on his/her plate so that the user can timely adjust the portion size before it is too late (e.g., the food cannot be returned to the food-serving storage once being placed on the user's plate).

Figure 2:
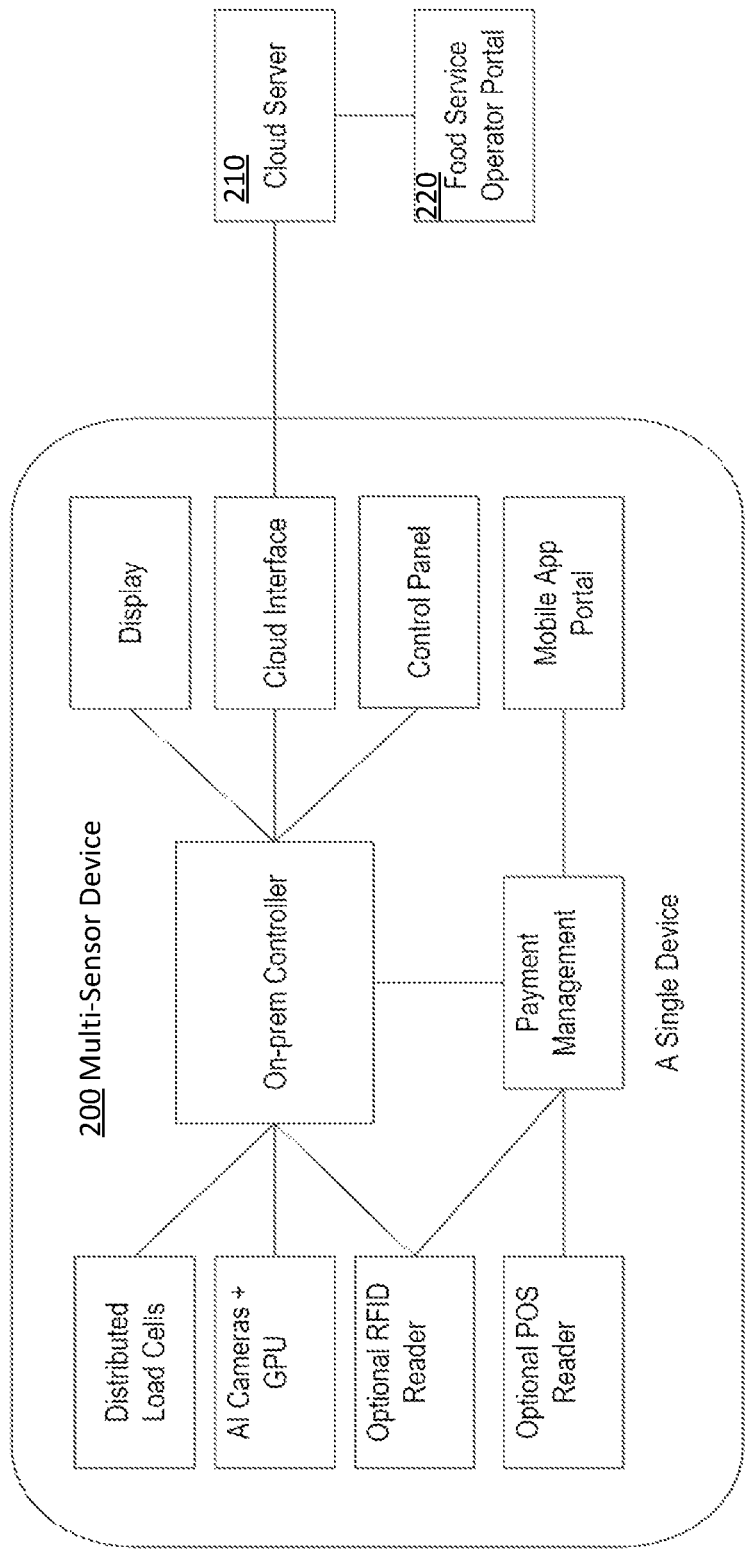
FIG. 2 illustrates a diagram of an exemplary system for instant dietary feedback using the AI-assisted multi-sensor device in accordance with some embodiments.

FIG. 2 illustrates a diagram of an exemplary system for instant dietary feedback using the AI-assisted multi-sensor device in accordance with some embodiments. The diagram in FIG. 2 includes a structural diagram of the AI-assisted multi-sensor device in FIG. 1 and other components interacting with the AI-assisted multi-sensor device. The system depicted in FIG. 2 is for illustrative purposes only. Depending on the implementation, the system may include fewer, more, or alternative components.

In some embodiments, the system may include an AI-assisted multi-sensor device 200, a cloud server 210, and a foodservice operator portal 220. In some embodiments, the cloud server 210 may be deployed as a central hub that hosts a plurality of clients (e.g., cafeterias, buffets, banquets, restaurants), in which each client may have one or more AI-assisted multi-sensor devices 200 installed to provide customers/users instant dietary feedbacks and perform dietary tracking. The cloud server 210 may be configured in a multi-tenant mode by sharing its computing and storage resources among the plurality of clients. The resource sharing among the clients may be dynamically adjusted or balanced depending on the real-time needs.

In some embodiments, the cloud server 210 may interact with the foodservice operator portal 220, from which an operator may configure the cloud server 210 or configure the multi-sensor devices 200 of different clients through the cloud server 210. The configuration of the multi-sensor devices 200 may include updating firmware, sending software updates such as updated machine learning models, detecting malfunctions, etc.

In some embodiments, the cloud server 210 may receive individual users' dietary behavioral data from the multi-sensor device 200 and store it in a database. The cloud server 210 may perform periodical data analysis to explore user dietary behavioral patterns and make recommendations. For example, the cloud server 210 may cluster a plurality of users into a plurality of dietary goal groups based on dietary goals set by the users and determine a population average for each dietary goal group. The population average may include an average frequency of food-intake activities, an average intake of calories, sugar, fiber, protein, etc. Based on the population averages, the cloud server 210 may generate dietary reports and make recommendations for an individual user based on the user's dietary behavioral data and the population average of the corresponding dietary goal group.

In some embodiments, the AI-assisted multi-sensor device 200 may include an on-prem controller to process data collected from various sensors, such as a scale coupled with a plurality of distributed load cells, AI cameras equipped with processing units (e.g., GPUs), RFID readers for scanning RFID tag data, etc. For example, the on-prem controller may receive weight readings from one or more distributed load cells to determine the weight of food that a user has placed on his plate. As another example, the on-prem controller may receive a series of images from the AI cameras to identify food and estimate the volume or weight of the food using machine learning. In some cases, the AI cameras may perform local data processing (e.g., by cropping the images using bounding boxes surrounding objects of interest), and send the processed data (e.g., the cropped images) to the on-prem controller for further analysis. As yet another example, the on-prem controller may receive the RFID tag data scanned by the RFID reader, which may include a unique identifier associated with a user. The on-prem controller may associate the unique identifier with the user's dietary data for later analysis or payment determination.

As shown in FIG. 2, the AI-assisted multi-sensor device 200 may further include an optional Point of Sale (POS) reader and a payment management component to process payment. For example, when making a payment, a user may first scan his RFID tag using the RFID reader on the AI-assisted multi-sensor device 200. The on-prem controller may retrieve the food information (e.g., nutrition information, price) of the food that has been taken by the user, and send such information to the payment management component. The user may then swipe or tap his/her payment card using the POS reader to provide payment information. The payment management component may subsequently charge the user based on the food information using the payment information. Alternatively, the payment may be made through a user's mobile application portal.

In some embodiments, the AI-assisted multi-sensor device 200 may further include a display for providing instant dietary feedbacks to users, a cloud interface for exchanging data with the cloud server 210, and a control panel for controlling or managing the AI-assisted multi-sensor device 200.

Figure 3:
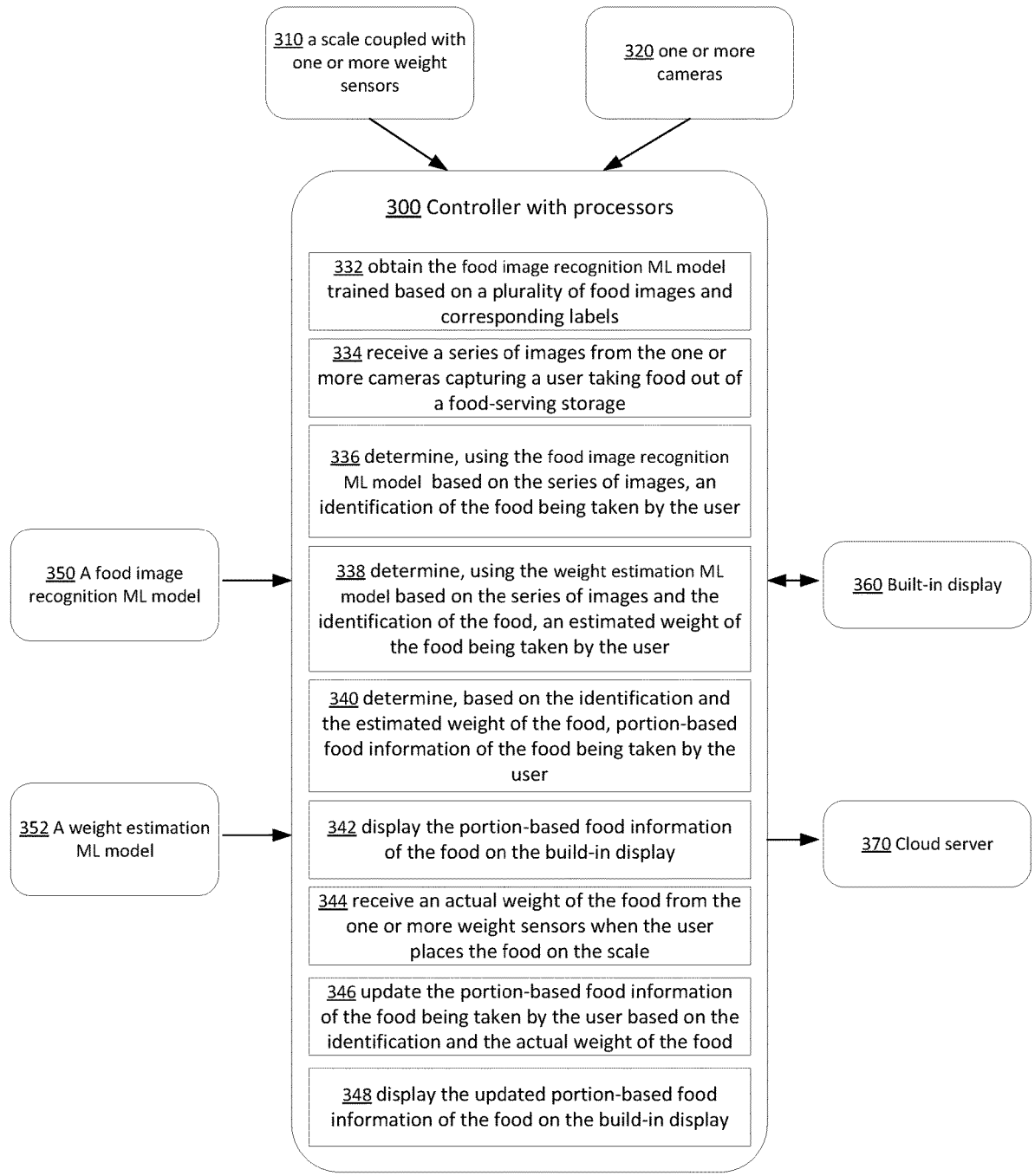
FIG. 3 illustrates an exemplary workflow diagram for generating instant dietary feedback using an AI-assisted multi-sensor device in accordance with some embodiments.

FIG. 3 illustrates an exemplary workflow diagram for generating instant dietary feedback using an AI-assisted multi-sensor device in accordance with some embodiments. In some embodiments, the AI-assisted multi-sensor device may include hardware components such as a scale coupled with one or more weight sensors 310, one or more cameras 320, a built-in display 360, and a controller 300 with processors. In some embodiments, the AI-assisted multi-sensor device may include software components such as a food image recognition machine learning (ML) model 350, a weight/volume estimation machine learning (ML) model 352, image processing pipelines (not shown in FIG. 3), etc. These hardware and software components may work collectively to monitor a user's food-taking activity, process the monitored data (e.g., image/video and weight readings), and provide users instant dietary feedback about the food to be consumed. The exemplary workflow illustrated in FIG. 3 includes an example use case of the AI-assisted multi-sensor device for generating instant dietary feedback.

In some embodiment, the controller 300 may obtain the food image recognition ML model 350 trained based on a plurality of food images and corresponding labels at step 332. Here, the "obtaining" may refer to receiving the trained model from another entity (e.g., an on-prem server or a cloud server 370), or training the model by the controller 300 itself. For example, the controller may receive a plurality of food images and proper labels as training data. The food images may be generated by scanning different types of food offered by a foodservice using the cameras 320. The scanning process may include displaying notifications for an operator to change different angles of the food until a progress indicator showing the scanning is complete. An operator may manually enter the labels for the food images.

Since the number of food served by one foodservice is usually small, manually labeling the scanned images may be acceptable. In some embodiments, each label may include an identification of the food (e.g., name or number). Based on these labeled training data, the controller may train a neural network for food identification based on food images. For instance, the neural network may include a feature extraction layer to detect the edges, shapes, locations, and colors in a food image, and an output layer with nodes corresponding to the different types of food. Each node may output a matching probability that the food in an input image matches with a food corresponding to the node. During the training process, a food image may be input into the neural network to obtain the matching probabilities from the nodes in the output layer. Based on a distance between the matching probabilities and the label of the food image, the parameters of the neural network may be adjusted to minimize the distance. In some embodiments, the distance may be determined as a Euclidean distance. In some embodiments, during the training process, the food along with its ingredients will be determined. The weight of the visible ingredients will be estimated coupled with the reading from the precision scale coupled with one or more weight sensors 310 to determine the actual label (portion size and weight) for training. Separate models (e.g., a different model from the food recognition model) may be used to predict the portion size and weight.

In some embodiments, the food image recognition ML model 350 may obtained through two-phase process, including (1) obtaining a generic model trained using food images obtained from the general domain (e.g., by using images from the Internet, or by an operator scanning food items at a centralized location (e.g., kitchen)) (2) deploying the generic model to the edge devices (e.g., AI-assisted multi-sensor device 200) installed on the stations; (3) performing on-device training to fine tune the generic model based on locally collected images using the on-device cameras. This approach is more effective than training-once-and-deploy approaches because the environment in which the device is located may be different from the kitchen environment (e.g., lightning, angle, etc.). The generic model may be fine tuned to improve accuracy based on the data collected from the current specific domain (i.e., domain adaptation). These locally collected data may be labeled periodically by the operator (like every day, every week). In other words, the food image recognition ML model 350 on the device is self-evolving by performing these periodic "on-device training" cycles.

In some embodiments, the controller 300 may receive a series of images from the one or more cameras 320 capturing a user taking food out of a food-serving storage (e.g., a food well at a buffet or cafeteria) at step 334. The series of images may include one or more 2D images, 3D images, or depth images of the food captured by the one or more cameras 320 from one or more viewing angles. If the user is using a serving utensil (ladle, scoop, pasta server, tong, spatula, etc.) to take food, the images may capture the utensil and the food held by the utensil. In some embodiments, the one or more cameras 320 may capture a video and the series of images may be extracted from the video.

In some embodiments, the controller 300 may determine an identification of the food being taken by the user at step 336. The determination may use the food image recognition ML model 350 based on the series of images. As described above, the food image recognition ML model 350 is trained to identify the food in an image. The output of the food image recognition ML model 350 may include one or more food candidates similar to the food in the image with corresponding matching probabilities. The food candidate with the highest probability may be determined as the identified food. In some embodiments, when the difference between the top two or more matching probabilities is below a threshold, the controller may display the corresponding top two or more food candidates on the built-in display 360 for the user to confirm the identification of the food. For example, while displaying the top two or more food candidates on the built-in display 360, the food candidate with the highest matching probability may be displayed in a highlighted manner to indicate that, without user selection, it will be treated as the identified food. In response to the user selecting a different food candidate, the display may be updated to indicate that the selected food candidate is the identified food.

In some embodiments, the food image recognition ML model 350 may further identify the ingredients in the food based on color, texture, shape, and other features extracted from the images. For example, a "dragon roll sushi" may include avocado, unagi, shrimp tempura, etc. However, depending on the restaurant, some dragon roll sushi may have different toppings such as sasames or fish roe. The images of the dragon roll sushi may include the corresponding colors from a particular angle, which allow the food image recognition ML model 350 to identify the ingredients. If the images show black/white toppings, the food image recognition ML model 350 may determine the dragon roll sushi has sasame rather than fish roe (orange color).

In some embodiments, the controller 300 may determine an estimated weight of the food being taken by the user at step 338. The determination may use the weight estimation ML model 352 based on the series of images. The weight estimation ML model 352 may include a trained deep neural network. For example, a first depth image of the food captured from a first view angle may be fed into the weight estimation ML model 352, which may generate a second depth image of the food from a second view angle that is opposite to the first view angle. This process may be repeated for other depth images to generate one or more depth image pairs (e.g., each pair includes two depth images from two opposite angles). Based on the one or more depth image pairs, a 3D representation of the food may be constructed. The 3D representation of the food may be used to generate an estimated volume of the food, which may be used as a basis to estimate the weight of the food. For example, the controller 330 may retrieve food information of the food from a database based on the identification of the food. The food information may include nutrition information, price, ingredients, weight information per serving, or even an estimated density of the food that is pre-computed. The controller 330 may determine the estimated weight of the food based on the estimated volume and the food information.

In some embodiments, the controller 300 may determine portion-based food information of the food based on the identification of the food and the estimated weight at step 340. As described above, the identification of the food may be used to retrieve the food information from a database, which may include the nutrition information (e.g., the amount of calories, protein, fiber, sugar, carbohydrate per serving size). The controller 300 may then determine the portion-based food information based on the retrieved food information and the estimated weight. Since the weight of the food at this point is estimated based on the images of the food being taken by the user, the portion-based food information at this step is also an estimation. This estimated portion-based food information may be displayed to the user while the user is taking food from the food well and before the user places the food on its plate at step 342. In many cases, once the food is placed on the user's plate, he/she is allowed to return the food back to the food well. Therefore, this instant dietary feedback may help the user to determine whether to adjust the portion size promptly.

In some embodiments, the controller 300 may receive an actual weight of the food from the one or more weight sensors when the user places the food on the scale 310 at step 344. The actual weight may be different from the estimated weight predicted by the weight estimation ML model 352. In this case, the controller 330 may update the portion-based food information of the food based on the actual weight and the food information at step 346. This updated portion-based food information may be displayed on the built-in display 360 to accurately reflect the nutrition information of the portion of food taken by the user at step 348. In some embodiments, the updated portion-based food information may include portion-based ingredient information, portion-based nutrition information, portion-based pricing information, and allergen information.

In some embodiments, the controller 300 may upload the updated portion-based food information to the cloud server 370 for data aggregation and further data analysis.

Figure 4:
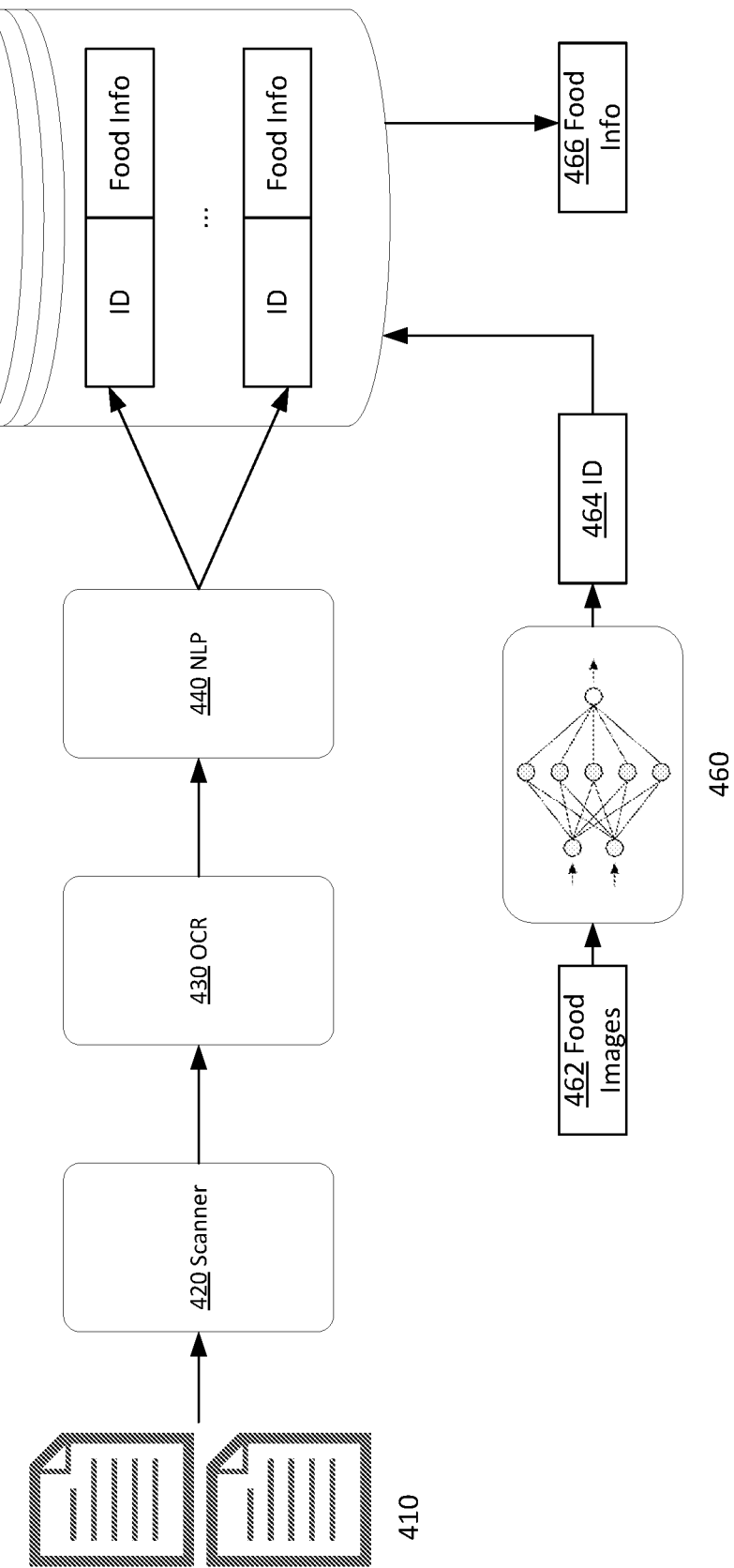
FIG. 4 illustrates an exemplary workflow diagram for constructing a food information database for the AI-assisted multi-sensor device in accordance with some embodiments.

FIG. 4 illustrates an exemplary workflow diagram for constructing a food information database 450 for the AI-assisted multi-sensor device in accordance with some embodiments. As described above, the food information database 450 may store a mapping between food identifications (e.g., names, numbers) and corresponding food information (e.g., price, nutrition, ingredients). The food information database 450 may be constructed in various ways. For example, an operator of a restaurant may manually enter the data in the food information database 450 as the number of food served by one restaurant may not be a large number. The workflow illustrated in FIG. 4 describes an automated way to construct the food information database 450.

In some embodiments, menus 410 may be scanned using a scanner 420 to generate scanned menus. The scanned menus may include the food names and ingredients and/or nutrition information of the food. The scanned menus may be converted into text using Optical Character Recognition (OCR) 430. Natural Language Processing (NLP) algorithms 440 may be used to extract the food names and the food information. The food names and corresponding food information may be stored in the database 450.

In some embodiments, after a series of food images 462 are input into a trained food identification neural network 460, the identifier (e.g., name) 464 of the food may be predicted. Based on the name 464 of the food, the corresponding food information 466 may be retrieved from the database 450.

Figure 5:
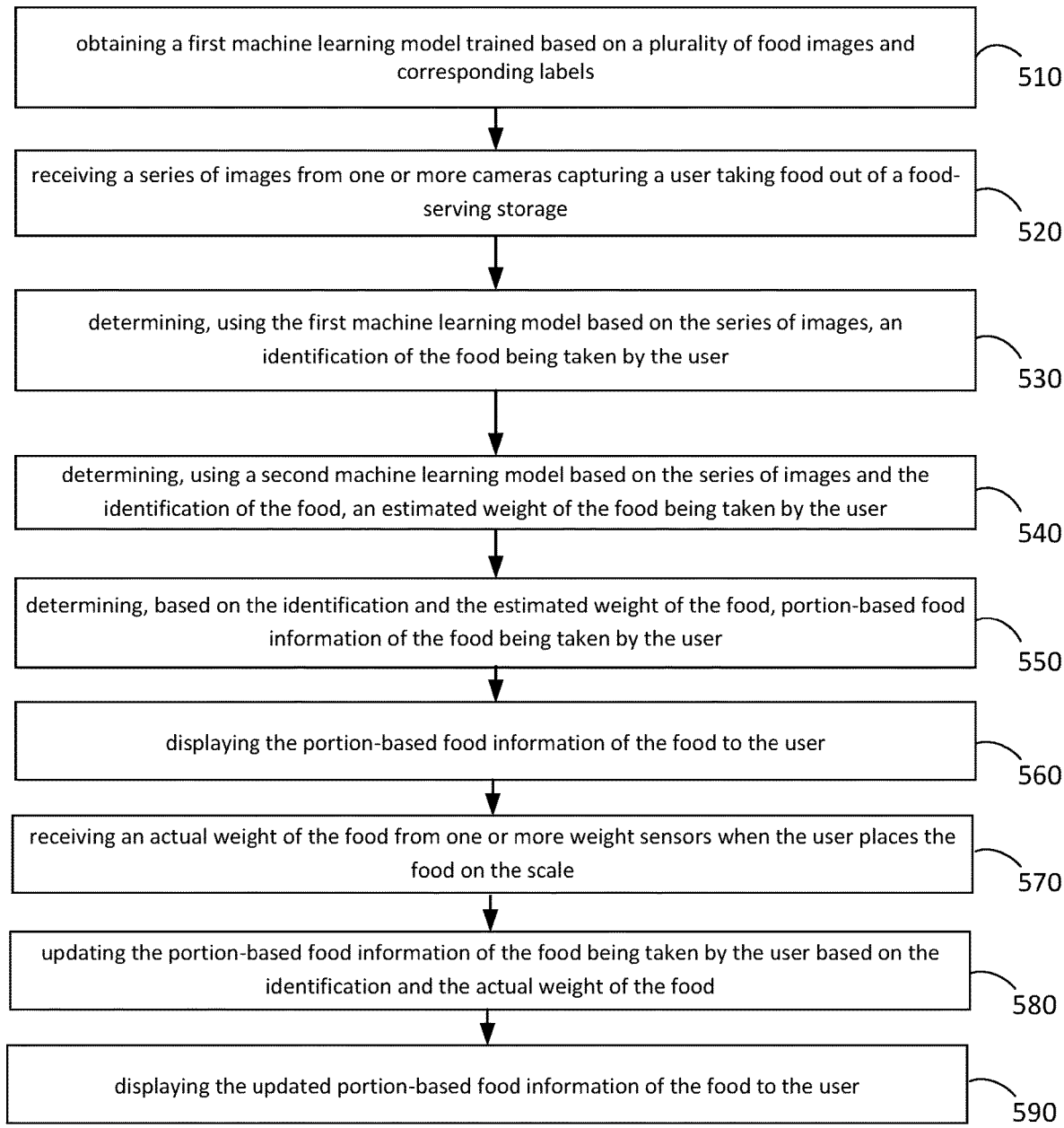
FIG. 5 illustrates an exemplary method for generating instant dietary feedback using the AI-assisted multi-sensor device in accordance with some embodiments.

FIG. 5 illustrates an exemplary method 500 for generating instant dietary feedback using the AI-assisted multi-sensor device in accordance with some embodiments. Method 500 may be performed by a computer device, apparatus, or system. The method 500 may be performed by one or more modules/components of the environment or system illustrated by FIGS. 1-4. The operations of the method 500 presented below are intended to be illustrative. Depending on the implementation, the method 500 may include additional, fewer, or alternative steps performed in various orders or parallel.

Block 510 includes obtaining a first machine learning model trained based on a plurality of food images and corresponding labels.

Block 520 includes receiving a series of images from one or more cameras capturing a user taking food out of a food-serving storage. In some embodiments, the series of images comprises one or more depth images of the food captured by the one or more cameras from one or more viewing angles. In some embodiments, the one or more cameras comprising one or more of the following: a depth sensor, a time of flight (ToF) camera, or a Light Detection and Ranging (LiDAR) camera.

Block 530 includes determining, using the first machine learning model based on the series of images, an identification of the food being taken by the user. In some embodiments, the determination includes: feeding the series of images into the first machine learning model to obtain one or more probabilities of one or more predicted identifications of the food; displaying the one or more predicted identifications on the display, with a first predicted identification with a highest probability being displayed as the identification of the food; and in response to a user selection of a second predicted identification from the one or more predicted identifications, updating the display by displaying the second predicted identification as the identification of the food.

Block 540 includes determining, using a second machine learning model based on the series of images and the identification of the food, an estimated weight of the food being taken by the user. In some embodiments, the determining of the estimated weight of the food being taken by the user using the second machine learning model comprises: inputting a first depth image of the food captured from a first view angle into the second machine learning model; receiving, from the second machine learning model, a second depth image of the food from a second view angle that is different from the first view angle; generating a 3D representation of the food being taken by the user based on the first depth image and the second depth image; obtaining an estimated volume of the food being taken by the user based on the 3D representation of the food; and determining the estimated weight of the food based on the estimated volume of the food and the identification of the food. In some embodiments, the second machine learning model comprises a trained deep neural network. In some embodiments, the determining of the estimated weight of the food being taken by the user includes: obtaining food information of the food from a database based on the identification of the food; and determining the estimated weight of the food based on the food information and the estimated volume.

Block 550 includes determining, based on the identification and the estimated weight of the food, portion-based food information of the food being taken by the user.

Block 560 includes displaying the portion-based food information of the food to the user Block 570 includes receiving an actual weight of the food from one or more weight sensors when the user places the food on the scale. In some embodiments, the portion-based food information comprises: portion-based ingredient information; portion-based nutrition information; portion-based pricing information; or allergen information.

Block 580 includes updating the portion-based food information of the food being taken by the user based on the identification and the actual weight of the food.

Block 590 includes displaying the updated portion-based food information of the food to the user.

In some embodiments, the method 500 may further include receiving the plurality of food images captured by the one or more cameras when an operator scans one or more food items using the one or more cameras; receiving the corresponding labels of the plurality of food images scanned by the operator; and training a neural network as the first machine learning model based on the plurality of food images and the corresponding labels for food identification. In some embodiments, the neural network comprises a layer for feature extraction and an output layer, the output layer comprising one or more nodes corresponding to the one or more food items. In some embodiments, the training of the neural network includes: inputting a food image into the neural network to obtain one or more matching probabilities corresponding to one or more matched food; and adjusting parameters of the neural network based on the one or more matching probabilities and a label corresponding to the food image.

In some embodiments, the method 500 may further include receiving a scanned menu from the one or more cameras; converting the scanned menu into text using Optical Character Recognition (OCR); extracting food identifications and corresponding food information from the text using Natural Language Processing (NLP), wherein the food identifications comprise food names; and storing the food identifications and the corresponding food information in a database. In some embodiments, the determining of the portion-based food information of the food being taken by the user includes: retrieving food information of the food from the database based on the identification, wherein the food information comprises nutrition information of the food; and determining the portion-based food information of the food based on the food information and the estimated weight.

Figure 6:
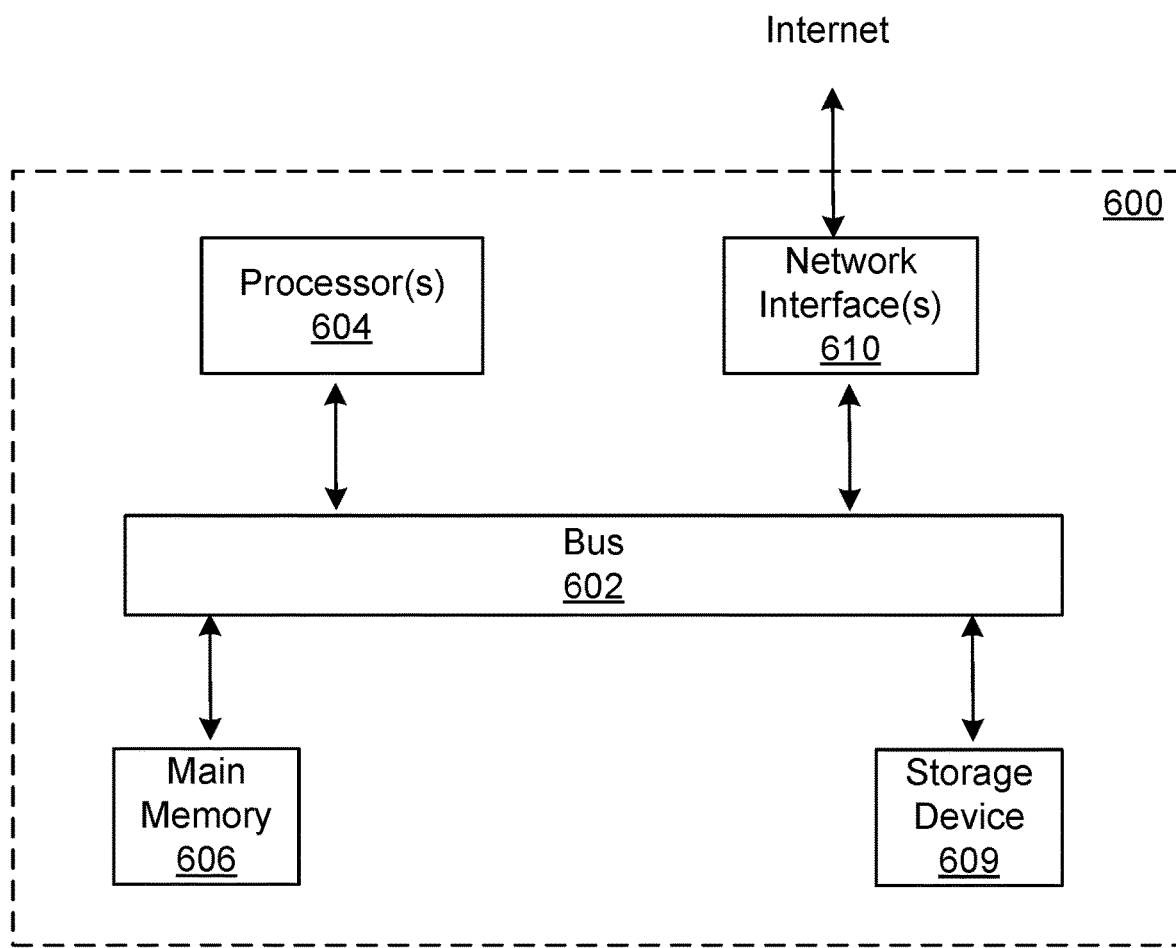
FIG. 6 illustrates an example computing device in which any of the embodiments described herein may be implemented.

FIG. 6 illustrates an example computing device in which any of the embodiments described herein may be implemented. The computing device may be used to implement one or more components of the systems and the methods shown in FIGS. 1-5. The computing device 600 may comprise a bus 602 or other communication mechanisms for communicating information and one or more hardware processors 604 coupled with bus 602 for processing information. Hardware processor(s) 604 may be, for example, one or more general-purpose microprocessors.

The computing device 600 may also include a main memory 606, such as a random-access memory (RAM), cache and/or other dynamic storage devices, coupled to bus 602 for storing information and instructions to be executed by processor(s) 604. Main memory 606 also may be used for storing temporary variables or other intermediate information during the execution of instructions to be executed by processor(s) 604. Such instructions, when stored in storage media accessible to processor(s) 604, may render computing device 600 into a special-purpose machine that is customized to perform the operations specified in the instructions. Main memory 606 may include non-volatile media and/or volatile media. Non-volatile media may include, for example, optical or magnetic disks. Volatile media may include dynamic memory. Common forms of media may include, for example, a floppy disk, a flexible disk, hard disk, solid-state drive, magnetic tape, or any other magnetic data storage medium, a CD-ROM, any other optical data storage medium, any physical medium with patterns of holes, a RAM, a DRAM, a PROM, and EPROM, a FLASH-EPROM, NVRAM, any other memory chip or cartridge, or networked versions of the same.

The computing device 600 may implement the techniques described herein using customized hard-wired logic, one or more ASICs or FPGAs, firmware and/or program logic which in combination with the computing device may cause or program computing device 600 to be a special-purpose machine. According to one embodiment, the techniques herein are performed by computing device 600 in response to processor(s) 604 executing one or more sequences of one or more instructions contained in main memory 606. Such instructions may be read into main memory 606 from another storage medium, such as storage device 609. Execution of the sequences of instructions contained in main memory 606 may cause processor(s) 604 to perform the process steps described herein. For example, the processes/methods disclosed herein may be implemented by computer program instructions stored in main memory 606. When these instructions are executed by processor(s) 604, they may perform the steps as shown in corresponding figures and described above. In alternative embodiments, hard-wired circuitry may be used in place of or in combination with software instructions.

The computing device 600 also includes a communication interface 610 coupled to bus 602. Communication interface 610 may provide a two-way data communication coupling to one or more network links that are connected to one or more networks. As another example, communication interface 610 may be a local area network (LAN) card to provide a data communication connection to a compatible LAN (or WAN component to communicated with a WAN). Wireless links may also be implemented.

Certain of the operations may be performed in a distributed manner among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Each process, method, and algorithm described in the preceding sections may be embodied in, and fully or partially automated by, code modules executed by one or more computer systems or computer processors comprising computer hardware. The processes and algorithms may be implemented partially or wholly in application-specific circuitry.

When the functions disclosed herein are implemented in the form of software functional units and sold or used as independent products, they can be stored in a processor-executable non-volatile computer-readable storage medium. Particular technical solutions disclosed herein (in whole or in part) or aspects that contribute to current technologies may be embodied in the form of a software product. The software product may be stored in a storage medium, comprising a number of instructions to cause a computing device (which may be a personal computer, a server, a network device, and the like) to execute all or some steps of the methods of the embodiments of the present application. The storage medium may comprise a flash drive, a portable hard drive, ROM, RAM, a magnetic disk, an optical disc, another medium operable to store program code, or any combination thereof.

Particular embodiments further provide a system comprising a processor and a non-transitory computer-readable storage medium storing instructions executable by the processor to cause the system to perform operations corresponding to steps in any method of the embodiments disclosed above. Particular embodiments further provide a non-transitory computer-readable storage medium configured with instructions executable by one or more processors to cause the one or more processors to perform operations corresponding to steps in any method of the embodiments disclosed above.

Embodiments disclosed herein may be implemented through a cloud platform, a server or a server group (hereinafter collectively the "service system") that interacts with a client. The client may be a terminal device, or a client registered by a user at a platform, wherein the terminal device may be a mobile terminal, a personal computer (PC), and any device that may be installed with a platform application program.

The various features and processes described above may be used independently of one another or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The exemplary systems and components described herein may be configured differently than described. For example, elements may be added to, removed from, or rearranged compared to the disclosed example embodiments.

The various operations of exemplary methods described herein may be performed, at least partially, by an algorithm. The algorithm may be comprised in program codes or instructions stored in a memory (e.g., a non-transitory computer-readable storage medium described above). Such algorithm may comprise a machine learning algorithm. In some embodiments, a machine learning algorithm may not explicitly program computers to perform a function but can learn from training data to make a prediction model that performs the function.

The various operations of exemplary methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

Certain of the operations may be performed in a distributed manner among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is in fact disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

As used herein, "or" is inclusive and not exclusive, unless expressly indicated otherwise or indicated otherwise by context. Therefore, herein, "A, B, or C" means "A, B, A and B, A and C, B and C, or A, B, and C," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context. Moreover, plural instances may be provided for resources, operations, or structures described herein as a single instance. Additionally, boundaries between various resources, operations, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

The term "include" or "comprise" is used to indicate the existence of the subsequently declared features, but it does not exclude the addition of other features. Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

What is claimed is:

1. A device for dietary tracking with feedback, comprising:
    a scale coupled with one or more weight sensors;
    one or more cameras;
    a display; and
    one or more processors coupled to the one or more weight sensors, one or more cameras, and display, and configured to:
        obtain a series of images from the one or more cameras capturing a movement of a user interacting with a food-serving storage;
        determine, based on movement features extracted from the series of images, whether the movement of the user is one of a food-taking action taking food out of the food-serving storage, a food-returning action returning food back to the food-serving storage, and refilling action;
        in response to the movement being the food-taking action, determine, by inputting the series of images into a first machine learning model, an identification of the food being taken by the user, wherein to determine the identification of the food, the one or more processors are further configured to:
            receive a plurality of food identification candidates generated by the first machine learning model, wherein the plurality of food identification candidates are associated with corresponding matching probabilities, and
            in response to a difference between the machine probabilities being below a threshold, display the plurality of food identification candidates on the display for the user to confirm;
        determine, by inputting the series of images and the identification of the food into a second machine learning model, an estimated weight of the food being taken by the user, wherein the determination of the estimated weight of the food being taken by the user comprises:
            feeding a first depth image of the food captured from a view angle into the second machine learning model;
            generating, by the second machine learning model, a second depth image of the food captured;
            constructing a 3D representation of the food based on the first depth image and the second depth image; and
            determining the estimated weight of the food based on the 3D representation of the food and the identification of the food;
        determine, based on the identification and the estimated weight of the food, first portion-based food information of the food being taken by the user;
        display the first portion-based food information of the food on the display;
        receive an actual weight of the food from the one or more weight sensors when the user places the food on the scale;
        update the first portion-based food information of the food being taken by the user with second portion-based food information determined based on the identification and the actual weight of the food; and
        display the second portion-based food information of the food on the display.

2. The device of claim 1, wherein the one or more processors are further configured to:
    receive the plurality of food images captured by the one or more cameras when an operator scans one or more food items using the one or more cameras;
    receive the corresponding labels of the plurality of food images scanned by the operator; and
    train a neural network as the first machine learning model based on the plurality of food images and the corresponding labels for food identification.

3. The device of claim 2, wherein the neural network comprises a layer for feature extraction and an output layer, the output layer comprising one or more nodes corresponding to the one or more food items.

4. The device of claim 2, wherein to train the neural network, the one or more processors are configured to:
    input a food image into the neural network to obtain one or more matching probabilities corresponding to one or more matched food; and
    adjust parameters of the neural network based on the one or more matching probabilities and a label corresponding to the food image.

5. The device of claim 1, wherein the first machine learning model is further trained to identify ingredients in the food by extracting color-based features from the series of images.

6. The device of claim 1, wherein to determine the estimated weight of the food, the one or more processors are configured to:
    obtain, based on the identification of the food, food information of the food from a database; and
    determine the estimated weight of the food based on the food information.

7. The device of claim 1, wherein to determine the identification of the food being taken by the user, the one or more processors are configured to:
    feed the series of images into the first machine learning model to obtain one or more probabilities of one or more predicted identifications of the food;

display the one or more predicted identifications on the display, with a first predicted identification with a highest probability being displayed as the identification of the food; and in response to a user selection of a second predicted identification from the one or more predicted identifications, update the display by displaying the second predicted identification as the identification of the food.

8. The device of claim 1, wherein the one or more processors are further configured to:
receive a scanned menu from the one or more cameras;
convert the scanned menu into text using Optical Character Recognition (OCR);
extract food identifications and corresponding food information from the text using Natural Language Processing (NLP), wherein the food identifications comprise food names; and
store the food identifications and the corresponding food information in a database.

9. The device of claim 8, wherein to determine the portion-based food information of the food being taken by the user based on the identification and the estimated weight of the food, the one or more processors are configured to:
retrieve, based on the identification, food information of the food from the database, wherein the food information comprises nutrition information of the food; and
determine the portion-based food information of the food based on the food information and the estimated weight.

10. The device of claim 1, wherein the one or more cameras comprising one or more of the following: a depth sensor, a time of flight (ToF) camera, or a Light Detection and Ranging (LiDAR) camera.

11. The device of claim 1, wherein the portion-based food information comprises:
portion-based ingredient information;
portion-based nutrition information;
portion-based pricing information; or
allergen information.

12. A computer-implemented method, comprising:
obtaining a series of images from one or more cameras capturing a movement of a user interacting with a food-serving storage;
determining, based on movement features extracted from the series of images, whether the movement of the user is one of a food-taking action taking food out of the food-serving storage, a food-returning action returning food back to the food-serving storage, and refilling action;
in response to the movement being the food-taking action, determining, by inputting the series of images into a first machine learning model, an identification of the food being taken by the user, wherein the determining comprises:
receiving a plurality of food identification candidates generated by the first machine learning model, wherein the plurality of food identification candidates are associated with corresponding matching probabilities, and
in response to a difference between the machine probabilities being below a threshold, displaying the plurality of food identification candidates on the display for the user to confirm;
determining, by inputting the series of images and the identification of the food into a second machine learning model, an estimated weight of the food being taken by the user, wherein the determination of the estimated weight of the food being taken by the user comprises:
feeding a first depth image of the food captured from a view angle into the second machine learning model;
generating, by the second machine learning model, a second depth image of the food captured;
constructing a 3D representation of the food based on the first depth image and the second depth image; and
determining the estimated weight of the food based on the 3D representation of the food and the identification of the food;
determining, based on the identification and the estimated weight of the food, first portion-based food information of the food being taken by the user;
displaying the first portion-based food information of the food on the display;
receive an actual weight of the food from one or more weight sensors when the user places the food on a scale;
updating the first portion-based food information of the food being taken by the user with second portion-based food information determined based on the identification and the actual weight of the food; and
displaying the second portion-based food information of the food on the display.

13. The method of claim 12, wherein the method further comprises:
receiving the plurality of food images captured by the one or more cameras when an operator scans one or more food items using the one or more cameras;
receiving the corresponding labels of the plurality of food images scanned by the operator; and
training a neural network as the first machine learning model based on the plurality of food images and the corresponding labels for food identification.

14. The method of claim 12, wherein the determining of the identification of the food being taken by the user comprises:
feeding the series of images into the first machine learning model to obtain one or more probabilities of one or more predicted identifications of the food;
displaying the one or more predicted identifications, with a first predicted identification with a highest probability being displayed as the identification of the food; and
in response to a user selection of a second predicted identification from the one or more predicted identifications, displaying the second predicted identification as the identification of the food to the user.

15. The method of claim 12, further comprising:
receiving a scanned menu from the one or more cameras;
converting the scanned menu into text using Optical Character Recognition (OCR);
extracting food identifications and corresponding food information from the text using Natural Language Processing (NLP), wherein the food identifications comprise food names; and
storing the food identifications and the corresponding food information in a database.

16. A non-transitory computer-readable storage medium, configured with instructions executable by one or more processors to cause the one or more processors to perform operations comprising:
obtaining a series of images from one or more cameras capturing a movement of a user interacting with a food-serving storage;
determining, based on movement features extracted from the series of images, whether the movement of the user is one of a food-taking action taking food out of the food-serving storage, a food-returning action returning food back to the food-serving storage, and refilling action;

in response to the movement being the food-taking action, determine, by inputting the series of images into a first machine learning model, an identification of the food being taken by the user, wherein the determining comprises:
- receiving a plurality of food identification candidates generated by the first machine learning model, wherein the plurality of food identification candidates are associated with corresponding matching probabilities, and
- in response to a difference between the machine probabilities being below a threshold, displaying the plurality of food identification candidates on the display for the user to confirm;

determining, by inputting the series of images and the identification of the food into a second machine learning model, an estimated weight of the food being taken by the user, wherein the determination of the estimated weight of the food being taken by the user comprises:
- feeding a first depth image of the food captured from a view angle into the second machine learning model;
- generating, by the second machine learning model, a second depth image of the food captured;
- constructing a 3D representation of the food based on the first depth image and the second depth image; and
- determining the estimated weight of the food based on the 3D representation of the food and the identification of the food;

determining, based on the identification and the estimated weight of the food, first portion-based food information of the food being taken by the user;

displaying the first portion-based food information of the food on the display;

receiving an actual weight of the food from one or more weight sensors when the user places the food on a scale;

updating the first portion-based food information of the food being taken by the user with second portion-based food information determined based on the identification and the actual weight of the food; and displaying the second portion-based food information of the food on the display.

17. The device of claim 1, wherein to display the first portion-based food information of the food on the display, the one or more processors are further configured to:
- display the first portion-based food information instantly after the food is taken from the food-serving storage and before the user puts the food on a food container, allowing the user to timely adjust an amount of the food being taken from the food-serving storage before putting the food on the food container.

18. The device of claim 1, wherein the one or more processors are further configured to:
- obtain a generic version of the first machine learning model trained using food images obtained from the general domain;
- deploy the generic version of the first machine learning model on the device at a food station;
- collect the plurality of food images captured by the one or more cameras as training data;
- periodically receive labels of the training data; and
- perform on-device training retraining to fine-tune the generic version of the first machine learning model based on the labels and the training data.

19. The device of claim 17, wherein to display the plurality of identification candidates on the display for the user to confirm, the one or more processors are further configured to:
- display a food identification with a highest matching probability in a highlighted manner to indicate that, without user selection, the food identification with the highest matching probability is treated as the identification of the food.

* * * * *